US009428527B2

(12) United States Patent
Hattori

(10) Patent No.: US 9,428,527 B2
(45) Date of Patent: Aug. 30, 2016

(54) SYMMETRIC HYPERBRANCHED TYPE SILICONE-MODIFIED POLYMERIZABLE COMPOUND, AND ITS MODULARIZED PREPARATION METHOD

(71) Applicant: SHIN-ETSU CHEMICAL CO., LTD., Tokyo (JP)

(72) Inventor: Hatsuhiko Hattori, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/773,942

(22) PCT Filed: Jan. 31, 2014

(86) PCT No.: PCT/JP2014/000503
§ 371 (c)(1),
(2) Date: Sep. 9, 2015

(87) PCT Pub. No.: WO2014/141578
PCT Pub. Date: Sep. 18, 2014

(65) Prior Publication Data

US 2016/0039848 A1 Feb. 11, 2016

(30) Foreign Application Priority Data

Mar. 15, 2013 (JP) ................................ 2013-053585
Dec. 25, 2013 (JP) ................................ 2013-266651

(51) Int. Cl.

| | |
|---|---|
| ***C07F 7/10*** | (2006.01) |
| ***C07F 7/08*** | (2006.01) |
| ***C07C 271/16*** | (2006.01) |
| ***C08G 77/38*** | (2006.01) |
| ***C08F 290/06*** | (2006.01) |
| ***C08G 83/00*** | (2006.01) |
| ***C08G 77/08*** | (2006.01) |
| ***C08G 77/46*** | (2006.01) |

(52) U.S. Cl.
CPC ........... *C07F 7/0849* (2013.01); *C07C 271/16* (2013.01); *C08F 290/068* (2013.01); *C08G 77/08* (2013.01); *C08G 77/38* (2013.01); *C08G 77/46* (2013.01); *C08G 83/005* (2013.01)

(58) Field of Classification Search
CPC .................................................... C07F 7/0849
USPC ........................................................ 556/420
See application file for complete search history.

(56) References Cited

U.S. PATENT DOCUMENTS

| | | | |
|---|---|---|---|
| 6,184,407 | B1 | 2/2001 | Yoshitake et al. |
| 6,306,992 | B1 | 10/2001 | Yoshitake et al. |
| 2003/0019209 | A1 | 1/2003 | Tsuruga et al. |
| 2006/0018935 | A1 | 1/2006 | Nishijima et al. |
| 2012/0269747 | A1 | 10/2012 | Iimura et al. |

FOREIGN PATENT DOCUMENTS

| | | | |
|---|---|---|---|
| JP | 2000-044579 | A | 2/2000 |
| JP | 2001-040093 | A | 2/2001 |
| JP | 4236342 | B2 | 3/2009 |
| JP | 4270607 | B2 | 6/2009 |
| JP | 4664062 | B2 | 4/2011 |
| JP | 4681881 | B2 | 5/2011 |
| WO | 02/055888 | A1 | 7/2002 |
| WO | 2008/093655 | A1 | 8/2008 |
| WO | 2011/049246 | A1 | 4/2011 |

OTHER PUBLICATIONS

ISA—PCT Search Report PCT/JP2014/000503.*
USPTO—STN Search Results.*
Hattori, Hatsuhiko et al., "Suzuki-Miyaura reaction in water, conducted by employing am amphiphilic dendritic phosphine-palladium catalyst: a positive dendritic effect on chemical yield", Tetrahedron Letters, 2007, vol. 48, pp. 6817-6820.
Nemoto, Hisao et al., "An Efficient and Practical Method for the Preparation of a Branched Oligoglycerol with Acetonide Protection Groups", Chemistry Letters, 2010, vol. 39, pp. 856-857.
Apr. 15, 2014 Search Report Issued in International Patent Application No. PCT/JP2014/000503.

* cited by examiner

*Primary Examiner* — Porfirio Nazario Gonzalez
*Assistant Examiner* — Kofi Adzamli
(74) *Attorney, Agent, or Firm* — Oliff PLC

(57) ABSTRACT

A symmetric hyperbranched type silicone-modified polymerizable compound contains a compound represented by the following general formula (1). A hyperbranched type silicone-modified polymerizable compound has flexibility at the branched skeleton itself than the conventional ones, and reactivity of a polymerizable functional group is good and it is positionally and sterically symmetric, while it has a highly branched structure having siloxane chains.

$$[(R^AR^B)_2CHOCH_2]_2CHOR^C{}_cR^D \quad (1)$$

$R^A$ represents a monovalent linear, branched or cyclic siloxane chain; $R^B$ represents a divalent hydrocarbonylene methylene ether group represented by $—CH_2CR^{b1}R^{b2}(CR^{b3}R^{b4})_{n1}OCH_2—$, each of $R^{b1}$, $R^{b2}$, $R^{b3}$ and $R^{b4}$ may be the same or different from each other and represents a hydrogen atom or a linear, branched or cyclic hydrocarbon group having 1 to 10 carbon atoms which may be bonded to each other, "n1" represents an integer selected from 0 to 10; $R^C$, a divalent linking group; "c", 0 or 1; and $R^D$, an unsaturated polymerizable functional group.

18 Claims, No Drawings

SYMMETRIC HYPERBRANCHED TYPE SILICONE-MODIFIED POLYMERIZABLE COMPOUND, AND ITS MODULARIZED PREPARATION METHOD

TECHNICAL FIELD

The present invention relates to a symmetric hyperbranched type silicone-modified polymerizable compound having a siloxane chain, a modularized preparation method of the polymerizable compound, and a silicone modified composition using the polymerizable compound.

BACKGROUND ART

It has well been known that a compound having a highly branched structure, for example, a dendrimer compound or a hyperbranched type polymer is markedly improved in functionality depending on its branched degree (Non-Patent Literature 1). As a preparation method of the compound having such a branched structure, there has been known mainly two methods, one of which is the convergent method, and the other is the divergent method. The convergent method is a method in which a branched state side chain is bonded to a core which locates at the center portion of a branched state compound at the final stage or near to the final stage, and has merits that purification of the side chain is relatively easy since it is a relatively low molecule, it is possible to introduce a high purity branched state side chain into the core and a branched state compound with high purity can be readily obtained. However, when a number of the branch at the side chain is large, there is a problem that apex of the side chain becomes bulky, so that reactivity to the core is lowered. In addition, the divergent method is a method in which a branch is successively extended to outward from the core, and when a branch in the side chain is omitted, compounds having different distributions are difficulty separated, so that a compound with good purity can be difficulty prepared. However, a branch is extended to the direction of the outside having a space so that there is a merit that lowering in reactivity due to steric hindrance is relatively a little whereby the reactivity is good.

Further, it has been disclosed that a dendrimer type siloxane having a branch has a low viscosity as compared to that of the conventional linear siloxane having the same number of the silicon atoms, and it becomes an excellent material as a mold releasing agent, a lubricant, a resin modifying agent, a crosslinking agent (Patent Literature 1). In addition, a siloxane dendrimer in which a dendrimer type siloxane is grafted to a polymerizable compound has been developed (Patent Literature 2). However, these siloxanes have narrow branched chain and are chemical structurally rigid so that they have poor flexibility, and as a grafted branched chain becomes larger (the generation is increased), there is a problem that an effect of steric hindrance appears, and reactivity of the polymerizable functional group becomes insufficient, whereby the third generation in which the branch becomes 3 units at one side chain has not yet been commercialized.

From the problems, it has been developed a method in which a siloxane chain had been tried to be introduced into an allyl ether compound ($CH_2{=}CHCH_2OR$) by hydrosilylation, but it has been known that in the olefins of the allyl ether compound, 10 to 20% thereof are internally rearranged to form a 1-propenyl ether product ($CH_3CH{=}CHOR$) which becomes a main accessory component, and it has also been known that propionaldehyde is generated when the 1-propenyl ether is hydrolyzed by a moisture, etc., in the air, and it becomes a cause of generating bad odor from the final product, etc. To solve the problem of the odor, it has been disclosed a method in which a vinyl ether group at the inside of the 1-propenyl ether is reduced to a propyl ether ($CH_3CH_2CH_2OR$) by a hydrogenation reaction using a hydrogen gas under pressure in an autoclave, whereby chemical decomposition is prevented and generation of bad odor is prohibited (Patent Literature 3), further, a method in which a solid acid is used at the time of a hydrogenation reaction whereby removal of generation of a bad odor substance can be realized, which solves the problem that an acetal is formed by reacting the decomposed aldehyde and an alcohol in some cases, and the acetal remains in the product without being reduced by the hydrogenation reaction, which gradually decomposes by a moisture or an acid, so that an odor from the product is continued to be released (Patent Literature 4), and a method in which propionaldehyde generated from a lower alcohol (R'OH) is subjected to an acetalizing treatment ($CH_3CH_2CH(OR')_2$) to make the bad odor component a low boiling point compound, which is removed by distillation (Patent Literature 5). However, these methods are coping methods for the purpose of suppressing generation of the bad odor component or removing the bad odor component, and are not the methods to basically suppress generation of an internal rearrangement product at the time of the reaction.

On the other hand, whereas it has been well known, it is possible to reduce an internal rearrangement product of the olefin at the time of a hydrosilylation reaction by using β-methallyl alcohol which is 2-methyl-2-propen-1-ol, but there are problems that a minutely produced isobutyraldehyde expels unpleasant odor, and further the cost of the β-methallyl alcohol used as a starting material is expensive as compared with that of the allyl alcohol.

Therefore, in a branched compound containing an ether bond having flexibility, it is difficult to synthesize a branched type siloxane with good purity due to the problem of the internal rearrangement, and when a silicone is tried to be introduced into the branched compound having an allyl group, if internal rearrangement of a byproduct of the hydrosilylation reaction is generated, the products one of which is a silicone chain symmetric cannot be obtained. When this is tried to be applied to pharmaceuticals, medical devices or foods, an asymmetric branched state compound is markedly affected to the effectiveness of the physiological activity due to the formation of the diastereomer in many cases. It has also been well known that it is a high degree of difficulty to introduce a positionally and sterically pure, and symmetric branched structure from the viewpoint of synthetic chemistry.

CITATION LIST

Patent Literature

PATENT LITERATURE 1: Japanese Patent No. 4,270,607

PATENT LITERATURE 2: Japanese Patent No. 4,236,342

PATENT LITERATURE 3: International Patent Laid-Open Publication No. 02/055888

PATENT LITERATURE 4: Japanese Patent No. 4,681,881

PATENT LITERATURE 5: Japanese Patent No. 4,664,062

Non-Patent Literature

NON-PATENT LITERATURE 1: Tetrahedron Letters, 2007, 48(38), 6817-6820

SUMMARY OF THE INVENTION

Technical Problem

The present invention has been done in view of the circumstances, and an object thereof is to provide a hyperbranched type silicone-modified polymerizable compound which has flexibility at the branched skeleton itself than the conventional ones, as well as reactivity of a polymerizable functional group is good and it is positionally and sterically symmetric, while it has a highly branched structure having siloxane chains.

Solution to Problem

To accomplish the objects, the present invention is to provide a symmetric hyperbranched type silicone-modified polymerizable compound which comprises a compound represented by the following general formula (1), $$[(R^AR^B)_2CHOCH_2]_2CHOR^C{}_cR^D \quad (1)$$

wherein $R^A$ represents a monovalent linear, branched or cyclic siloxane chain; $R^B$ represents a divalent hydrocarbonylene methylene ether group represented by $—CH_2CR^{b1}R^{b2}(CR^{b3}R^{b4})_{n1}OCH_2—$, each of $R^{b1}$, $R^{b2}$, $R^{b3}$ and $R^{b4}$ may be the same or different from each other and represents a hydrogen atom or a linear, branched or cyclic hydrocarbon group having 1 to 10 carbon atoms which may be bonded to each other, "n1" represents an integer selected from 0 to 10; $R^C$ represents a divalent linking group; "c" represents 0 or 1; and $R^D$ represents an unsaturated polymerizable functional group.

Such a symmetric hyperbranched type silicone-modified polymerizable compound is employed, the product can be made a material having flexibility at the branched skeleton itself than the conventional ones and reactivity of a polymerizable functional group can be made good by introducing an oligoglycerin having an ether group at the branch, while it has a highly branched structure having siloxane chains.

Among these, in the divalent hydrocarbonylene methylene ether groups represented by $R^B$ in the general formula (1), "n1" represents an integer selected from 1 to 10, and when "n1" represents 1, $R^{b1}$ is preferably a hydrocarbon group having 1 to 10 carbon atoms and $R^{b2}$ is preferably a hydrogen atom.

By introducing such a divalent hydrocarbonylene methylene ether group, a symmetric hyperbranched type silicone-modified polymerizable compound having better reactivity of a polymerizable functional group, being positionally and sterically symmetric and having more pure branched structure can be obtained.

It is also preferred that the divalent linking group represented by $R^C$ in the general formula (1) is any of the linking group selected from divalent linking groups represented by $—XR^Y{}_yR^ZO—$, $—XR^Y{}_yCR^{Z'}R^{Z''}O—$, and an oligoalkylene oxy group having a repeating unit whose number of repetition is an integer of 1 to 10, the repeating unit having 2 to 10 carbon atoms.

wherein X represents any one selected from $—CH_2—$, $—C(=O)—$ and $—C(=S)—$; $R^Y$ represents a divalent functional group containing 0 or 1 atom selected from a nitrogen atom, an oxygen atom, a sulfur atom or a carbon atom; $R^Z$ represents a linear, branched or cyclic alkylene group having 2 to 10 carbon atoms which may be substituted by an oxygen atom(s); "y" represents an integer selected from 0 or 1; and $R^{Z'}$ and $R^{Z''}$ each represent an alkyl group having 1 to 10 carbon atoms.

By introducing such a divalent linking group, a symmetric hyperbranched type silicone-modified polymerizable compound having more flexibility can be obtained.

In addition, the present invention is a process for preparing the symmetric hyperbranched type silicone-modified polymerizable compound, and which provides a modularized preparation method which comprises preparing the compound represented by the general formula (1) by subjecting a compound represented by the following general formula (2) and an intermediate represented by the following general formula (3) to a hydrosilylation reaction, $$R^{A'} \quad (2)$$

wherein $R^{A'}$ represents a linear, branched or cyclic siloxane having one reactive hydrogen group in the molecule, hereinafter sometimes abbreviated to as H-siloxane, $$(R^{B'}{}_2CHOCH_2)_2CHOR^C{}_cR^D \quad (3)$$

wherein $R^{B'}$ represents a monovalent hydrocarbonylene methylene ether group having a double bond at the terminal thereof and represented by $CH_2=CR^{b1}(CR^{b3}R^{b4})_{n1'}OCH_2—$, where $R^{b1}$, $R^{b3}$ and $R^{b4}$ have the same meanings as defined above, "n1'" represents an integer selected from 0 to 10; and $R^c$, "c" and $R^D$ have the same meanings as defined above.

At this time, "n1'" in the general formula (3) is preferably an integer selected from 1 to 10.

When such a modularized preparation method is employed, generation of an internal rearrangement product of the olefin can be suppressed, and a symmetric hyperbranched type silicone-modified polymerizable compound with high purity can be prepared more efficiently than the conventional ones.

Among these, in the hydrosilylation reaction, it is preferred that a catalyst is used, and the compound represented by the general formula (2) is used in an amount of 0.80 to 1.00 mole % based on the terminal alkenylene group of the intermediate represented by the general formula (3).

By preparing the intermediate as mentioned above, generation of an internal rearrangement product of the olefin can be more suppressed.

Also, the catalyst to be used in the hydrosilylation reaction is preferably a transition metal catalyst.

Further, the transition metal catalyst is preferably a platinum catalyst.

Thus, in the modularized preparation method of the present invention, a transition metal catalyst, in particular, a platinum catalyst can be suitably used in the hydrosilylation reaction.

It is also preferred that the intermediate represented by the general formula (3) is prepared by reacting the compound represented by the following general formula (4) and the compound represented by the following general formula (5) or the compound represented by the following general formula (6), $$(R^{B'}{}_2CHOCH_2)_2CHOH \quad (4)$$

wherein $R^{B'}$ has the same meaning as defined above, $$R^{C'}R^D \quad (5)$$

wherein $R^D$ has the same meaning as defined above, and $R^{C'}$ represents a monovalent reactive group, $$R^{D'} \quad (6)$$

wherein $R^{D'}$ represents an unsaturated polymerizable compound having a reactive functional group.

When such a modularized preparation method is employed, a symmetric hyperbranched type silicone-modified polymerizable compound can be prepared without impairing reactivity of a polymerizable functional group.

Moreover, it is preferred that the monovalent reactive group represented by $R^{C'}$ in the general formula (5) is any of the reactive group selected from a monovalent reactive group represented by $X{=}R^{Y'}R^ZO$—, T-X—$R^Y{}_yR^ZO$—, $X{=}R^{Y'}CR^{Z'}R^{Z''}O$—, T-X—$R^Y{}_yCR^{Z'}R^{Z''}O$—, and an oligoalkylene oxy group having a repeating unit whose number of repetition is an integer of 1 to 10, the repeating unit having 2 to 10 carbon atoms, which has a reactive group at the one terminal, wherein X, $R^Y$, $R^Z$, "y", $R^{Z'}$ and $R^{Z''}$ have the same meanings as defined above, $R^{Y'}$ represents a trivalent functional group containing 0 or 1 of any atom selected from a nitrogen atom, an oxygen atom, a sulfur atom and a carbon atom, and T represents a hydroxyl group or any atom selected from a chlorine atom and a bromine atom.

When such a modularized preparation method is employed, a symmetric hyperbranched type silicone-modified polymerizable compound having higher flexibility can be prepared.

At this time, it is preferred that $R^D$ in the general formula (5) is a monovalent unsaturated polymerizable functional group selected from an acrylic group, a methacrylic group, an alkynyl group, a styryl group, an indenyl group, an alkenyl group, a cycloalkenyl group, a norbornyl group, a conjugated or non-conjugated alkadiene group and a vinyl ether group each of which may contain a linear, branched or cyclic substituent having 1 to 10 carbon atoms which contains a hetero atom(s).

At this time, $R^{D'}$ of the general formula (6) is preferably an unsaturated polymerizable compound which contains a material in which an unsaturated group selected from any of an acrylic group, a methacrylic group, an alkynyl group, a styryl group, an indenyl group, an alkenyl group, a cycloalkenyl group, a norbornyl group, a conjugated or non-conjugated alkadiene group and a vinyl ether group each of which may contain a linear, branched or cyclic substituent having 1 to 10 carbon atoms which contains a hetero atom(s), and a reactive functional group selected from any of a hydroxyl group, an amino group, a hydroxycarbonyl group, an aldehyde group, an acid halide group, an ester group, a haloformate group, a halogenated alkyl group, an isocyanate group, an isothiocyanate group, a ketene group, a phosphate group, an epoxy group, an aziridine group, a tosyl group, a mesyl group, a trifluoromethanesulfonyl group, a bromane group, an iodane group, a halogenated aryl group and a nitroaryl group are directly bonded, or bonded through a linking group in the molecule.

When such a modularized preparation method is employed, a symmetric hyperbranched type silicone-modified polymerizable compound can be prepared easily without impairing reactivity of the polymerizable functional group.

Further, it is the modularized preparation method, and in the reaction of the compound represented by the general formula (4) and the compound represented by the general formula (5) or the compound represented by the general formula (6), it is preferred to use one or more kinds of catalysts comprising a Lewis acid selected from any of an inorganic or organic tin complex, titanium complex, iron complex, copper complex, zinc complex, aluminum complex, zirconium complex, yttrium complex, scandium complex, indium complex, lanthanum complex, cerium complex, samarium complex, europium complex, silicon complex; or a tertiary organic base, and to use the catalyst in an amount of 0.001 to 0.500 mole % based on the amount of the compound represented by the general formula (4).

The modularized preparation method of the present invention may employ such a catalyst.

Advantageous Effects of Invention

When the symmetric hyperbranched type silicone-modified polymerizable compound of the present invention is employed, the product can be made a material having flexibility at the branched skeleton itself than the conventional ones and reactivity of a polymerizable functional group can be made good by introducing an oligoglycerin having an ether group at the branch, while it has a highly branched structure having a siloxane chain. In addition, when the modularized preparation method of the present invention is employed, a symmetric hyperbranched type silicone-modified polymerizable compound can be prepared more efficiently while generation of an internal rearrangement product of the olefin is further suppressed.

DESCRIPTION OF EMBODIMENTS

The present inventor has intensively studied to solve the problems, and as a result, the person has found that by introducing siloxane chains in the presence of a catalyst into a branched type polymerizable compound which can be obtained by bonding a compound having a plural number of glycerin skeletons, i.e., symmetric oligoglycerin skeletons as branched structures with a polymerizable compound in the presence of a catalyst, a branched type polymerizable compound having more flexible branched skeleton itself than the conventional ones since it has an ether bond at the branch, while it is a highly branched structure having a siloxane chain, i.e., a symmetric hyperbranched type silicone-modified polymerizable compound can be obtained, whereby the present invention has been accomplished.

That is, the present invention relates to a symmetric hyperbranched type silicone-modified polymerizable compound (hereinafter sometimes abbreviated to as HB silicone) containing a compound represented by the following general formula (1), $$[(R^AR^B)_2CHOCH_2]_2CHOR^C{}_cR^D \quad (1)$$

wherein $R^A$ represents a monovalent linear, branched or cyclic siloxane chain; $R^B$ represents a divalent hydrocarbonylene methylene ether group represented by $—CH_2CR^{b1}R^{b2}(CR^{b3}R^{b4})_{n1}OCH_2—$, each of $R^{b1}$, $R^{b2}$, $R^{b3}$ and $R^{b4}$ may be the same or different from each other and represents a hydrogen atom or a linear, branched or cyclic hydrocarbon group having 1 to 10 carbon atoms which may be bonded to each other, "n1" represents an integer selected from 0 to 10; $R^C$ represents a divalent linking group; "c" represents 0 or 1; and $R^D$ represents an unsaturated polymerizable functional group.

When such a HB silicone is employed, the product can be made a material having flexibility at the branched skeleton itself than the conventional ones and reactivity of a polymerizable functional group can be made good by introducing an oligoglycerin having an ether group at the branch, while it has a highly branched structure having siloxane chains.

The HB silicone is preferably made that in the divalent hydrocarbonylene methylene ether groups represented by $R^B$ in the general formula (1), "n1" is made an integer selected from 1 to 10, and when "n1" represents 1, $R^{b1}$ represents a hydrocarbon group having 1 to 10 carbon atoms and $R^{b2}$ represents a hydrogen atom, to improve reactivity of the polymerizable functional group, to be positionally and sterically symmetric and to have more pure branched structure.

When such a divalent hydrocarbonylene methylene ether group is introduced, generation of an internal rearrangement product of an olefin which becomes the problem at the time of preparation mentioned later can be suppressed, and the product can be made a HB silicone with more pure and high purity.

Further, to make the material having more flexibility, the divalent linking group represented by $R^C$ in the general formula (1) is preferably made a linking group selected from any of a divalent linking group represented by $—XR^Y{}_yR^ZO—$, $—XR^Y{}_yCR^{Z'}R^{Z''}O—$, and an oligoalkylene oxy group having a repeating unit whose number of repetition is an integer of 1 to 10, the repeating unit having 2 to 10 carbon atoms wherein X represents any one selected from $—CH_2—$, $—C(═O)—$ and $—C(═S)—$, $R^Y$ represents a divalent functional group containing 0 or 1 atom selected from a nitrogen atom, an oxygen atom, a sulfur atom or a carbon atom, $R^Z$ represents a linear, branched or cyclic alkylene group having 2 to 10 carbon atoms which may be substituted by an oxygen atom(s), "y" represents an integer selected from 0 or 1, and $R^{Z'}$ and $R^{Z''}$ each represent an alkyl group having 1 to 10 carbon atoms.

As the preparation method of the HB silicone of the present invention, there may be exemplified by a method utilizing the convergent method which is one of the synthetic method of a dendrimer compound explained at the technical background. First, tetraallyl $[(CH_2═CHCH_2OCH_2)_2CHOCH_2]_2CHOH$, and a linear state siloxane $Bu[Si(CH_3)_2O]_4SiH(CH_3)_2$ which is a H-siloxane or $[(CH_3)_3SiO]_2SiH(CH_3)$ which is a branched state H-siloxane are subjected to a hydrosilylation reaction to obtain a linear state hydrosilylated product $[[Bu[Si(CH_3)_2O]_4Si(CH_3)_2(CH_2)_3OCH_2]_2CHOCH_2]_2CHOH$ or a branched state hydrosilylated product $[[[(CH_3)_3SiO]_2Si(CH_3)(CH_2)_3OCH_2]_2CHOCH_2]_2CHOH$. Next, the linear state or branched state hydrosilylated product and a polymerizable group-containing isocyanate $OCN(CH_2)_2OC(═O)C(CH_3)═CH_2$ are subjected to a carbamating reaction using an organometallic complex catalyst and an additive, and a synthetic method of the HB silicone is considered.

However, in the latter carbamating reaction, various inorganic or organic metal complex catalysts, reaction temperatures and additive were investigated, but steric hindrance of the secondary hydroxyl group at the apex in the linear or branched hydrosilylated product was large so that a carbamic acid ester was difficulty formed, and due to the strong conditions, gelation was generated by the reaction of the polymerizable groups. In addition, in the former hydrosilylation reaction, measurement by $^1H$-NMR was carried out as monitoring, and the reaction was stopped when the signal of the allyl group disappeared and the products were analyzed. As a result, an internal rearrangement product $(CH_3CH═CHOR)$ of the olefin was generated at a part of the allyl group $(CH_2═CHCH_2OR)$, so that a product into which four siloxane chains have been introduced was obtained with a little amount, and compounds into which three or two siloxane chains have been introduced were prepared as main products. Thus, according to the preparation method, while the HB silicone of the present invention could be obtained, but it could not be prepared with good efficiency and high purity.

Accordingly, the present inventor has investigated a preparation method using the divergent method. That is, first, the tetraallyl and the polymerizable isocyanate are previously reacted to form a carbamic acid ester $[(CH_2═CHCH_2OCH_2)_2CHOCH_2]_2CHOC(═O)NH(CH_2)_2OC(═O)C(CH_3)═CH_2$, then, the carbamic acid ester and a linear state or a branched state H-siloxane are subjected to a hydrosilylation reaction to obtain a linear state hydrosilylated product $[[Bu[Si(CH_3)_2O]_4Si(CH_3)_2(CH_2)_3OCH]_2]_2CHOCH_2CHOC(═O)NH(CH_2)_2OC(═O)C(CH_3)═CH_2$ or a branched state hydrosilylated product $[[[(CH_3)_3SiO]_2Si(CH_3)(CH_2)_3OCH_2]_2CHOCH_2]_2CHOC(═O)NH(CH_2)_2OC(═O)C(CH_3)═CH_2$.

The reaction of the tetraallyl and the polymerizable isocyanate proceeds by using a catalyst exemplified by an organoiron complex catalyst, whereby a carbamic acid ester derivative can be prepared. Further, when the obtained carbamic acid ester derivative is subjected to a hydrosilylation reaction with a linear state or a branched state H-siloxane in the presence of a platinum catalyst, then, the product can be prepared with better efficiency than that of the preparation method using the convergent method whereas an internal rearrangement product of the olefin is partially generated. The present inventor has intensively studied in view of the results, and as a result, the person reached the modularized preparation method of the present invention.

That is, the HB silicone of the present invention is preferably prepared by a modularized preparation method which comprises subjecting a compound represented by the following general formula (2) and an intermediate represented by the following general formula (3) to a hydrosilylation reaction to prepare the compound represented by the general formula (1), $$R^{A'} \tag{2}$$

wherein $R^{A'}$ represents a linear, branched or cyclic siloxane having one reactive hydrogen group in the molecule, $$(R^{B'}{}_2CHOCH_2)_2CHOR^C{}_cR^D \tag{3}$$

wherein $R^{B'}$ represents a monovalent hydrocarbonylene methylene ether group having a double bond at the terminal thereof and represented by $CH_2═CR^{b1}(CR^{b3}R^{b4})_{n1}$, $OCH_2—$, where $R^{b1}$, $R^{b3}$ and $R^{b4}$ have the same meanings as defined above, "n1'" represents an integer selected from 0 to 10; and $R^C$, "c" and $R^D$ have the same meanings as defined above.

Here, the term modularized means, in the constitution that there are several building blocks which become basic constitutional elements, a product is to be prepared by combining these building blocks freely in combination, and when the preparation method is employed, an improvement suitable for the uses can be done by selecting suitable building blocks to give a product, and it is possible to market a product rapidly.

In the following, best mode of the modularized preparation method of the present invention is explained.

I) Process for Preparing Intermediate Represented by the General Formula (3)

The intermediate represented by the general formula (3) is preferably prepared by reacting a compound represented by the following general formula (4) and a compound represented by the following general formula (5) or a compound represented by the following general formula (6), $$(R^{B'}{}_2CHOCH_2)_2CHOH \quad (4)$$

wherein $R^{B'}$ has the same meaning as defined above, $$R^{C'}R^{D} \quad (5)$$

wherein $R^{D}$ has the same meaning as defined above, and $R^{C'}$ represents a monovalent reactive group, $$R^{D'} \quad (6)$$

wherein $R^{D'}$ represents an unsaturated polymerizable compound having a reactive functional group.

Here, $R^{B'}$ in the general formula (4) which is one of the starting materials is a monovalent hydrocarbonylene methylene ether group having a double bond at the terminal thereof and represented by $CH_2{=}CR^{b1}(CR^{b3}R^{b4})_{n1}$, $OCH_2$—, and "n1'" in thereof is an integer selected from 0 to 10, preferably 1 to 10, further preferably 1 to 5 in the point that it is readily available. If it is an integer selected from 1 to 10, it is more preferred since internal rearrangement of the olefin can be further more effectively suppressed. Moreover, when it is such a group that $R^{b1}$ is a methyl group or a hydrogen atom, $R^{b3}$ and $R^{b4}$ are hydrogen atoms and "n1" represents an integer selected from 1 or 2, it is particularly preferred since generation of an internal rearrangement product of the olefin can be more effectively suppressed.

Also, CHOH in the general formula (4) is a 2-substituted methanol, and CHO in the same formula is a derivative of the 2-substituted methanol. That is, as the $R^{B'}{}_2CHO$ portion in the general formula (4), there may be mentioned glycerol-α,α'-di-3-butenyl ether (hereinafter sometimes abbreviated to as GDBE), glycerol-α,α'-di-4-pentenyl ether (hereinafter sometimes abbreviated to as GDPE), glycerol-α,α'-di-5-hexenyl ether (hereinafter sometimes abbreviated to as GDHE), glycerol-α,α'-di-6-heptenyl ether (hereinafter sometimes abbreviated to as GDHpE), glycerol-α,α'-dimethallyl ether (hereinafter sometimes abbreviated to as GDME), and glycerol-α,α'-diisoprenyl (3-methyl-3-butenyl) ether (hereinafter sometimes abbreviated to as GDiPE). By reacting these $R^{B'}{}_2CHO$ portion and epichlorohydrin, etc., the compound represented by the general formula (4) can be obtained.

Here, as alkenyl alcohols which become a starting material of the 2-substituted methanol portion and the 2-substituted methanol derivative in the general formula (4), 3-buten-1-ol (trade name: 3B1OL) or 4-penten-1-ol (trade name: 4P1OL) available from Hokko Chemical Industry Co., Ltd., 5-hexen-1-ol, 6-hepten-1-ol or β-methallyl alcohol available from Tokyo Chemical Industry Co., Ltd., and isoprenol (3-methyl-3-buten-1-ol) available from Merck may be used and other chain lengths than the above can be obtained by optionally synthesizing. For example, ethyl-4-methyl-4-pentenoate available from Sigma-Aldrich Japan Co., L.L.C., is reduced by using lithium aluminum hydride ($LiAlH_4$) to simply and easily obtain 4-methyl-4-penten-1-ol. Also, the compound having a cyclic or side chain longer than 2 carbon atoms can be obtained, for example, by oxidizing 1,4-dihydroxycyclohexane available from Tokyo Chemical Industry Co., Ltd., etc., using by a general method such as PCC and Swern oxidation, etc., and subjecting to Wittig reaction with triphenylmethyl phosphonium bromide and a base to obtain 4-methylenecyclohexan-1-ol. The $R^{B'}{}_2CHOH$ portion of the 2-substituted methanol in the general formula (4) can be obtained by the method in which an alcohol having an unsaturated bond selected from these alkenyl alcohols is heated at 45° C. and stirred with epichlorohydrin available from Tokyo Chemical Industry Co., Ltd., potassium hydroxide available from Merck and tetrabutylammonium bromide available from Tokyo Chemical Industry Co., Ltd., as a catalyst by applying thereto the same synthetic method disclosed in Chemistry Letters 2011, 39(8), pp. 856-857 by Nemoto, Hattori, et., al., then, the mixture is neutralized by hydrochloric acid, washed with water, and the volatile components are distilled off.

As the preparation method of the compound represented by the general formula (4), there may be mentioned the method in which $R^{B'}{}_2CHOH$ (3.5 equivalents) which corresponds to the starting material, epichlorohydrin (1.0 equivalent) available from Tokyo Chemical Industry Co., Ltd., potassium hydroxide (3.2 equivalents) available from Merck and tetrabutylammonium bromide (0.2 equivalent) available from Tokyo Chemical Industry Co., Ltd., as a catalyst are used, and the mixture is heated at 60° C. and stirred by applying thereto the same synthetic method disclosed in Chemistry Letters 2011, 39(8), pp. 856-857 by Nemoto, Hattori, et., al., then, the mixture is neutralized by hydrochloric acid, washed with water, and the volatile components are distilled off.

$R^{D}$ in the general formula (5) is preferably a monovalent unsaturated polymerizable functional group selected from any of an acrylic group, a methacrylic group, an alkynyl group, a styryl group, an indenyl group, an alkenyl group, a cycloalkenyl group, a norbornyl group, a conjugated or non-conjugated alkadiene group and a vinyl ether group each of which may contain a linear, branched or cyclic substituent having 1 to 10 carbon atoms which contains a hetero atom(s).

$R^{C'}$ in the general formula (5) is a monovalent reactive group, and preferably any of the reactive group selected from a monovalent reactive group represented by $X{=}R^{Y'}R^{Z}O$—, $T\text{-}X$—$R^{Y}{}_yR^{Z}O$—, $X{=}R^{Y'}CR^{Z'}R^{Z''}O$—, $T\text{-}X$—$R^{Y}{}_yCR^{Z'}R^{Z''}O$—, and an oligoalkylene oxy group having a repeating unit whose number of repetition is an integer of 1 to 10, the repeating unit having 2 to 10 carbon atoms, which has a reactive group at the one terminal:

wherein X, $R^{Y}$, $R^{Z}$, "y", $R^{Z'}$ and $R^{Z''}$ have the same meanings as defined above, $R^{Y'}$ represents a trivalent functional group containing 0 or 1 of any atom selected from a nitrogen atom, an oxygen atom, a sulfur atom and a carbon atom, and T represents a hydroxyl group or any atom selected from a chlorine atom and a bromine atom.

As the compound represented by the general formula (5) ($R^{C'}R^{D}$), there may be mentioned an isocyanate group-containing radical polymerizable compound, an isothiocyanate group-containing radical polymerizable compound, a ketene group-containing radical polymerizable compound, a chloromethyl group-containing radical polymerizable compound and an oligoalkylene oxide-containing radical polymerizable compound.

Among these, as the isocyanate group-containing radical polymerizable compound, those optionally synthesized may be used, or a commercially available product(s) may be used. As the commercially available products, there may be mentioned, for example, a (meth)acrylic type compound having an isocyanate such as Karenz MOI [$OCN(CH_2)_2OC({=}O)C(CH_3){=}CH_2$], Karenz MOI-EG [$OCN(CH_2)_2O(CH_2)_2OC({=}O)C(CH_3){=}CH_2$] or Karenz AOI [$OCN(CH_2)_2OC({=}O)CH{=}CH_2$] all available from Showa Denko K.K., and 3-isopropenyl-α,α-dimethylbenzyl isocyanate available from Tokyo Chemical Industry Co., Ltd., etc. In addition, when typical examples in the case of using the synthesized products are mentioned, an isocyanate group-containing radical polymerizable compound can be obtained by making a carboxylic acid compound having a corresponding polymerizable group a mixed acid anhydride using i-butyl, chloroformate or pivaloyl chloride, etc., acid-azidating the resulting material by reacting with sodium azide, and heating and stirring the obtained acid azide to carry out Curtius rearrangement, or by heating and stirring an alkylamine compound having a corresponding polymerizable group and triphosgene at 40° C.

As the isothiocyanate group-containing radical polymerizable compound, an optionally synthesized material is used and, for example, an isothiocyanate group-containing radical polymerizable compound can be obtained by making an alkyl alcohol having 1 to 10 carbon atoms having a corresponding polymerizable group a compound having an eliminable group by chlorinating it with oxalyl chloride or thionyl chloride, brominating it with carbon tetrabromide or boron tribromide, iodating it with N-iodosuccinimide or sodium iodide, tosylating it with p-toluenesulfonyl chloride and triethylamine or mesylating it with methanesulfonyl chloride and triethylamine, then, reacting the resulting material with potassium thiocyanate.

As the ketene group-containing radical polymerizable compound, an optionally synthesized material is used and it is $CH_2{=}C(CH_3)C({=}O)O{-}R^1{-}C{=}C{=}O$ wherein $R^1$ represents a linear, branched or cyclic alkylene group having 1 to 6 carbon atoms which may contain an oxygen atom, and 3-(1-oxoprop-1-enyl) methacrylate, 4-(1-oxobut-1-enyl) methacrylate, 5-(1-oxopent-1-enyl) methacrylate, 6-(1-oxohex-1-enyl) methacrylate, 7-(1-oxohept-1-enyl) methacrylate, 8-(1-oxooct-1-enyl) methacrylate, 6-(2-ethyl-1-oxohex-1-enyl) methacrylate and 2-(3-oxoprop-2-en-1-oxy) ethyl methacrylate are specifically mentioned. A synthetic method thereof is explained by referring to $CH_2{=}C(CH_3)C({=}O)OCH_2CH{=}C{=}O$ as an example, it can be synthesized by oxidizing a commercially available $CH_2{=}C(CH_3)C({-}O)O(CH_2)_3OH$ with chromic acid or Jones reagent, etc., reacting the resulting carboxylic acid $CH_2{=}C(CH_3)C({=}O)O(CH_2)_2C({=}O)OH$ with a chlorinating agent such as thionyl chloride, oxalyl chloride, triphosgene, phosgene, phosphoryl chloride, etc., to prepare an acid chloride $CH_2{=}C(CH_3)C({=}O)O(CH_2)_2C({=}O)Cl$, and then, treating it with a medium degree basic tertiary organic base such as triethylamine, etc.

As the chloromethyl group-containing radical polymerizable compound, an optionally synthesized material is used and the synthetic method thereof may be mentioned, for example, that methacrylic acid and anhydrous sodium carbonate are reacted to prepare potassium methacrylate, and then, bromochloromethane is added thereto as such whereby chloromethyl methacrylate can be simply and easily synthesized. Or else, 2-hydroxyethyl methacrylate (HEMA) and sodium hydride are reacted to prepare a sodium salt, and then, bromochloromethane is added thereto as such whereby 2-(chloromethoxy)ethyl methacrylate can be simply and easily synthesized. Thus, a hydroxyl group is present in the polymerizable group, the objective compound can be simply and easily synthesized.

As the oligoalkylene oxide-containing radical polymerizable compound, an optionally synthesized material may be used, or a commercially available product may be used. As the commercially available product, there may be mentioned 2-hydroxyethyl methacrylate, ethylene glycol monoacetacetate monomethacrylate, ethylene glycol monovinyl ether, diethylene glycol monovinyl ether all available from Tokyo Chemical Industry Co., Ltd., The oligoalkylene oxide-containing radical polymerizable compound having a reactive functional group can be obtained by 4-nitrophenyl carbonylating one terminal at the hydroxyl group side of a material using 4-nitrophenyl chloroformate, the material may be mentioned a poly- or oligoalkylene oxide in which one terminal of the polymerizable group is a methacryl group and another terminal of which is a hydroxyl group such as Blemmer PE-90, Blemmer PE-200, Blemmer PE-350, Blemmer PP-1000, Blemmer PP-800, Blemmer PP-500, Blemmer 50PEP-300, Blemmer 70PEP-350B, Blemmer 55PEP-800, Blemmer 10PEP-500B all available from NOF Corporation, and a poly- or oligoalkylene oxide in which one terminal of the polymerizable group is an acrylic group and another terminal of which is a hydroxyl group such as Blemmer AE-90, Blemmer AE-200, Blemmer AE-400, Blemmer AP-150, Blemmer AP-400, Blemmer AP-550, Blemmer AP-800, etc.

In the materials exemplified by the above, the compound represented by the general formula (5) ($R^{C'}R^{D}$) is more preferably a polymerizable group having a reactive functional group selected from an isocyanate group-containing acrylate, an isocyanate group-containing methacrylate, an isocyanate group and an ethylene glycol group-containing methacrylate, a thioisocyanate group-containing acrylate, a thioisocyanate group-containing methacrylate, a ketene group-containing acrylate, a ketene group-containing methacrylate, a chloromethyl group-containing acrylate, a chloromethyl group-containing methacrylate, or an oligoalkylene oxide-containing methacrylate, particularly preferably a polymerizable group having a reactive functional group selected from an isocyanate group-containing acrylate, an isocyanate group-containing methacrylate, an isocyanate group and an ethylene glycol group-containing methacrylate, a thioisocyanate group-containing acrylate.

Also, the unsaturated polymerizable compound having a reactive group of $R^{D'}$ of the general formula (6) is preferably an unsaturated polymerizable compound which contains a material in which an unsaturated group selected from any of an acrylic group, a methacrylic group, an alkynyl group, a styryl group, an indenyl group, an alkenyl group, a cycloalkenyl group, a norbornyl group, a conjugated or non-conjugated alkadiene group and a vinyl ether group each of which may contain a linear, branched or cyclic substituent having 1 to 10 carbon atoms which contains a hetero atom(s), and a reactive functional group selected from any of a hydroxyl group, an amino group, a hydroxycarbonyl group, an aldehyde group, an acid halide group (an acid chloride group, an acid bromide group, an acid iodide group, etc.), an ester group, a haloformate group (a chloroformate group, a bromoformate group, etc.), a halogenated alkyl group (a chloroalkyl group, a bromoalkyl group, an iodoalkyl group, etc.), an isocyanate group, an isothiocyanate group, a ketene group, a phosphate group, an epoxy group, an aziridine group, a tosyl group, a mesyl group, a trifluoromethanesulfonyl group, a bromane group, an iodane group, a halogenated aryl group (a chloroaryl group, a bromoaryl group, an iodoaryl group, etc.) and a nitroaryl group are directly bonded, or through a linking group in the molecule, or a commercially available product may be used. As the commercially available product, there may be mentioned methacrylic acid, methacrylic acid chloride, glycidyl methacrylate, acrylic acid, acrylic acid chloride, chloromethylstyrene, 4-vinylbenzoic acid, 2-chlorostyrene, 3-chlorostyrene, 4-chlorostyrene, 2-bromostyrene, 3-bromostyrene, 4-bromostyrene, 2-chloromethylstyrene, 3-chloromethylstyrene, 4-chloromethylstyrene, 2-bromomethylstyrene, 3-bromomethylstyrene, 4-bromomethyl-styrene, 1,3-butadiene, 1,3-pentadiene, 1,4-pentadiene, 1,3-hexadiene, 1,4-hexadiene, 1,5-hexadiene, 1,3-heptadiene, 1,4-heptadiene, 1,5-heptadiene, 1,6-heptadiene, 3-butyn-1-ol, 4-pentyn-1-ol, 5-hexyn-1-ol, 9-decyn-1-ol, 10-undecen-1-ol, propiolic acid, 5-hexynoic acid all available from Tokyo Chemical Industry Co., Ltd., or 2-hydroxypropyl acrylate (trade name: HPA), 4-hydroxybutyl acrylate (trade name: 4-HBA) both available from Osaka Organic Chemical Industry Ltd., and among these, acrylic acid chloride and methacrylic acid chloride are particularly preferred.

At the time of reacting the compound represented by the general formula (4) and the compound represented by the general formula (5) or the compound represented by the general formula (6), a catalyst may be used. Such a catalyst is preferably one or more kinds of Lewis acids selected from any of an inorganic or organic tin complex, titanium complex, iron complex, copper complex, zinc complex, aluminum complex, zirconium complex, yttrium complex, scandium complex, indium complex, lanthanum complex, cerium complex, samarium complex, europium complex and silicon complex, or tertiary organic bases and is preferably used in an amount of 0.001 to 0.500 mole % based on the amount of the compound represented by the general formula (4).

The inorganic or organic tin compound may be mentioned dibutyl tin dilaurate, dibutyl tin maleate, dibutyl tin phthalate, dibutyl tin dioctanoate, dibutyl tin bis(2-ethylhexanoate), dibutyl tin bis(methylmaleate), dibutyl tin bis(ethylmaleate), dibutyl tin bis(butyl-maleate), dibutyl tin bis (octylmaleate), dibutyl tin bis(tridecylmaleate), dibutyl tin bis(benzylmaleate), dibutyl tin diacetate, dibutyl tin bisisooctylthioglycolate, dibutyl tin bis-2-ethylhexylthioglycolate, dioctyl tin bis(ethylmaleate), dioctyl tin bis(octylmaleate), dibutyl tin dimethoxide, dibutyl tin bis(nonylphenoxide), dibutenyl tin oxide, dibutyl tin oxide, dibutyl tin bis(acetylacetonate), dibutyl tin bis(ethylacetacetonate), a reaction product of dibutyl tin oxide and a silicate compound, a reaction product of dibutyl tin oxide and a phthalic acid ester, etc.

The inorganic or organic titanium complex catalyst may be mentioned, for example, tetrabutyl titanate, tetrapropyl titanate, tetraisopropyl titanate, titanium tetrakis(acetylacetonate), titanium diisopropoxybis(acetylacetonate), titanium diisopropoxybis(ethylacetate), or a complex in which a diol such as tartaric acid, etc., is reacted with titanium chloride, etc.

The inorganic or organic iron complex catalyst may be mentioned iron chloride, iron bromide, iron acetyl-acetonate, iron triflate, iron acetate, iron pyridine complex, iron bipyridyl complex, iron terpyridyl complex, iron pincer complex, iron imine complex, iron salen complex, iron tetramethylenediamine complex, iron ethylenediamine complex, iron ephedrine complex, iron carbonyl complex, iron dienyl complex, ferrocene complex, etc.

The inorganic or organic copper complex catalyst may be mentioned copper chloride, copper bromide, copper acetylacetonate, copper triflate, copper acetate, copper pyridine complex, copper bipyridyl complex, copper pincer complex, copper imine complex, copper salen complex, copper tetramethylenediamine complex, copper ethylenediamine complex, copper ephedrine complex, copper carbonyl complex, copper dienyl complex, etc.

The inorganic or organic zinc complex catalyst may be mentioned zinc chloride, zinc bromide, zinc chloride, zinc bromide, zinc acetylacetonate, zinc triflate, zinc acetate, zinc pyridine complex, zinc bipyridyl complex, zinc terpyridyl complex, zinc pincer complex, zinc imine complex, zinc salen complex, zinc tetramethylenediamine complex, zinc ethylenediamine complex, zinc ephedrine complex, zinc carbonyl complex, zinc dienyl complex, etc.

The inorganic or organic aluminum complex catalyst may be mentioned aluminum chloride, aluminum bromide, aluminum acetylacetonate, aluminum triflate, aluminum acetate, aluminum pyridine complex, aluminum bipyridyl complex, aluminum pincer complex, aluminum imine complex, aluminum salen complex, aluminum tetramethylenediamine complex, aluminum ethylenediamine complex, aluminum ephedrine complex, methylaluminoxane (commonly known as MAO) which is prepared by adding water to trimethyl aluminum, etc.

The inorganic or organic zirconium complex catalyst may be mentioned zirconium chloride, zirconium bromide, zirconium acetylacetonate, zirconium triflate, zirconium acetate, zirconium pyridine complex, zirconium bipyridyl complex, zirconium terpyridyl complex, zirconium pincer complex, zirconium imine complex, zirconium salen complex, zirconium tetramethylenediamine complex, zirconium ethylenediamine complex, zirconium ephedrine complex, zirconium carbonyl complex, zirconium dienyl complex, zirconocene chloride, etc.

The inorganic or organic yttrium complex catalyst may be mentioned yttrium chloride, yttrium bromide, yttrium acetylacetonate, yttrium triflate, yttrium acetate, yttrium pyridine complex, yttrium bipyridyl complex, yttrium terpyridyl complex, yttrium pincer complex, yttrium imine complex, yttrium salen complex, yttrium tetramethylenediamine complex, yttrium ethylenediamine complex, yttrium ephedrine complex, yttrium carbonyl complex, yttrium dienyl complex, etc.

The inorganic or organic scandium complex catalyst may be mentioned scandium chloride, scandium bromide, scandium acetylacetonate, scandium carbonate, scandium triflate, scandium acetate, scandium pyridine complex, scandium bipyridyl complex, scandium terpyridyl complex, scandium pincer complex, scandium imine complex, scandium salen complex, scandium tetramethylenediamine complex, scandium ethylenediamine complex, scandium ephedrine complex, scandium carbonyl complex, scandium dienyl complex, etc.

The inorganic or organic indium complex catalyst may be mentioned indium chloride, indium bromide, indium acetylacetonate, indium triflate, indium acetate, indium pyridine complex, indium bipyridyl complex, indium pincer complex, indium imine complex, indium salen complex, indium tetramethylenediamine complex, indium ethylenediamine complex, indium ephedrine complex, indium carbonyl complex, etc.

The inorganic or organic lanthanum complex catalyst may be mentioned lanthanum chloride, lanthanum bromide, lanthanum acetylacetonate, lanthanum triflate, lanthanum acetate, lanthanum pyridine complex, lanthanum bipyridyl complex, lanthanum terpyridyl complex, lanthanum pincer complex, lanthanum imine complex, lanthanum salen complex, lanthanum tetramethylenediamine complex, lanthanum ethylenediamine complex, lanthanum ephedrine complex, lanthanum carbonyl complex, lanthanum dienyl complex, etc.

The inorganic or organic cerium complex catalyst may be mentioned cerium chloride, cerium bromide, cerium carbonate, cerium acetylacetonate, cerium triflate, cerium acetate, cerium pyridine complex, cerium bipyridyl complex, cerium terpyridyl complex, cerium pincer complex, cerium imine complex, cerium salen complex, cerium tetramethylenediamine complex, cerium ethylenediamine complex, cerium ephedrine complex, cerium carbonyl complex, cerium dienyl complex, etc.

The inorganic or organic samarium complex catalyst may be mentioned samarium chloride, samarium bromide, samarium iodide cerium carbonate, samarium acetylacetonate, samarium triflate, samarium acetate, samarium pyridine complex, samarium bipyridyl complex, samarium terpyridyl complex, samarium pincer complex, samarium imine complex, samarium salen complex, samarium tetramethylenediamine complex, samarium ethylenediamine complex, samarium ephedrine complex, samarium carbonyl complex, samarium dienyl complex, etc.

The inorganic or organic europium complex catalyst may be mentioned europium chloride, europium bromide, europium iodide cerium carbonate, europium acetylacetonate, europium triflate, europium acetate, europium pyridine complex, europium bipyridyl complex, europium terpyridyl complex, europium pincer complex, europium imine complex, europium salen complex, europium tetramethylenediamine complex, europium ethylenediamine complex, europium ephedrine complex, europium carbonyl complex, europium dienyl complex, etc.

The inorganic or organic silicon complex catalyst may be mentioned silicon chloride, silicon bromide, silicon carbonate, silicon acetylacetonate, silicon triflate, silicon acetate, silicon pyridine complex, silicon bipyridyl complex, silicon terpyridyl complex, silicon pincer complex, silicon imine complex, silicon salen complex, silicon tetramethylenediamine complex, silicon ethylenediamine complex, silicon ephedrine complex, silicon carbonyl complex, silicon dienyl complex, etc. The silicon complex may be mentioned trimethylsilyl triflate.

Also, the tertiary organic base may be mentioned trimethylamine, triethylamine ($Et_3N$), diisopropylethylamine (DIPEA), tri-n-butylamine, tri-n-pentylamine, tri-n-hexylamine, tri-n-heptylamine, tri-n-octylamine, N-methylpyrrolidine, N-methylpiperidine, N-methylmorpholine (NMO), N,N,N',N'-tetramethylethylenediamine (TMEDA), N-methylimidazole (NMI), pyridine, 2-methylpyridine, 3-methylpyridine, 4-methylpyridine, 2,6-lutidine, 1,3,5-collidine, N,N-dimethylaminopyridine (DMAP), pyrazine, quinoline, 1,8-diazabicyclo-[5,4,0]-7-undecene (DBU), 1,4-diazabicyclo-[2,2,2]octane (DABCO), etc. In this reaction, more preferred are tetraisopropyl titanate, dibutyl tin dilaurate, iron acetylacetonate and $Et_3N$, and the most preferred in the above is iron acetylacetonate.

A catalyst amount of the catalyst to be used is preferably 0.001 to 0.500 mole % based on the amount of the compound represented by the general formula (4), more preferably 0.005 to 0.050 mole %. If it is 0.001 mole % or more, the reaction likely proceeds, while if it is 0.500 mole % or less, the reaction system is not colored so that it is preferred. The most preferred is in the range of 0.005 to 0.01 mole % in consideration with toxicity and reactivity.

In the reaction, it may be carried out without any solvent or with a solvent. When the solvent is used, the solvent to be used is preferably an aprotic solvent(s) which may be used alone or in admixture, and preferably selected from a substituted or unsubstituted aromatic hydrocarbon compound having 6 to 12 carbon atoms which contains a hydrocarbon group selected from 1 to 6 carbon atoms, a substituted or unsubstituted saturated alicyclic hydrocarbon compound having 5 to 12 carbon atoms which contains a linear, branched or cyclic hydrocarbon group selected from 1 to 6 carbon atoms, a linear, branched or cyclic amide compound in which a linear, branched or cyclic hydrocarbon having 1 to 8 carbon atoms may be substituted on the nitrogen, a linear, branched or cyclic ether compound having 1 or 2 oxygen atoms in which a linear, branched or cyclic, saturated or unsaturated hydrocarbon having 1 to 8 carbon atoms may be each independently substituted on the oxygen atom(s), a linear, branched or cyclic alkylnitrile having 1 to 6 carbon atoms, and a linear, branched or cyclic, saturated or unsaturated halogenated hydrocarbon compound having 1 to 10 carbon atoms.

Examples of such a solvent may be selected from, for example, toluene, o-xylene, m-xylene, p-xylene, 1,3,5-mesitylene, 1,2,3-mesitylene, 1,2,4-mesitylene, ethylbenzene, n-propylbenzene, i-propylbenzene, n-butylbenzene, i-butylbenzene, sec-butylbenzene, t-butylbenzene, n-pentylbenzene, i-pentylbenzene, sec-pentylbenzene, t-pentylbenzene, n-hexylbenzene, hexylbenzene, sec-hexylbenzene, t-hexylbenzene, cyclopentane, cyclohexane, cycloheptane, cyclooctane, methylcyclohexane, ethylcyclohexane, propylcyclohexane, n-butylcyclohexane, i-butylcyclohexane, sec-butylcyclohexane, t-butylcyclohexane, n-pentylcyclohexane, i-pentylcyclohexane, sec-pentylcyclohexane, t-pentylcyclohexane, n-hexylcyclohexane, i-hexylcyclohexane, sec-hexylcyclohexane, t-hexylcyclohexane, limonene, N,N'-dimethylformamide (DMF), N,N'-dimethylformacetamide (DMAc), N-methylpyrrolidone (NMP), 1,3-dimethyl-2-imidazolidinone (DMI), 1,3-dimethyl-3,4,5,6-tetrahydro-2(1H)-pyrimidinone (DMPU), dimethylsulfoxide (DMSO), diethyl ether, t-butyl methyl ether (TBME), dibutyl ether, cyclopentyl methyl ether (CPME), diphenyl ether, tetrahydrofuran (THF), tetrahydropyran (THP), 1,4-dioxane, 2-methyltetrahydrofuran, 2-ethyltetrahydrofuran, acetonitrile, propionitrile, butyronitrile, benzonitrile, α,α,α-trifluoromethylbenzene, chlorobenzene, chloroform, dichloromethane and 1,2-dichloroethane, more preferably toluene, ethylbenzene, methylcyclohexane or ethylcyclohexane, and most preferably toluene or without the solvent.

II) Process for Introducing Siloxane Chain into Intermediate Represented by the General Formula (3)

The compound represented by the general formula (1) contained in the HB silicone of the present invention is preferably a material obtained by subjecting the compound represented by the general formula (2) ($R^{A'}$) and the intermediate represented by the general formula (3) obtained by the method to a hydrosilylation reaction.

As $R^{A'}$ of the compound represented by the general formula (2), it is not particularly limited so long as it is a siloxane having one reactive hydrogen in the molecule (H-siloxane), and may be any structure of a linear, branched or cyclic.

In the hydrosilylation reaction, it is preferred to use a suitable amount of the H-siloxane, more preferably 0.90 to 1.00 mole equivalent of the H-siloxane is used based on one terminal alkenyl group of the intermediate represented by the general formula (3), further preferably 0.95 to 1.00 mole equivalent of the H-siloxane is used based on one terminal alkenyl group. In the present invention, suppression of the internal rearrangement product of the olefin in the hydrosilylation reaction can be realized, so that adjustment of the used amount of the H-siloxane, in particular, reduction thereof becomes easy, whereby a sufficient effect can be exerted with an amount of the H-siloxane as mentioned above.

Also, in the hydrosilylation reaction, the catalyst may be used singly or by diluting with a solvent, etc., and it is preferably a transition metal catalyst, more preferably a platinum catalyst. Such a platinum catalyst may be preferably selected from chloroplatinic acid hexahydrate [Speier catalyst], a Karstedt's catalyst ($Pt_2[[(CH_2{=}CH)(CH_3)_2Si]_2O]_3$), an Ashby's catalyst ($Pt_4[CH_2{=}CHSi(CH_3)O]_4$) and a Lamoreaux catalyst (a Pt-octanal/octanol complex), and the most preferred catalyst is a Karstedt's catalyst or an Ashby's catalyst in consideration with readily available and reactivity.

In the hydrosilylation reaction, it may be carried out without solvent or by using a solvent. When the solvent is to be used, it is preferably selected from a substituted or unsubstituted aromatic hydrocarbon compound having 6 to 12 carbon atoms containing a hydrocarbon group selected from 1 to 6 carbon atoms, a substituted or unsubstituted saturated alicyclic hydrocarbon compound having 5 to 12 carbon atoms which contains a linear, branched or cyclic hydrocarbon group having 1 to 6 carbon atoms, a linear, branched or cyclic amide compound in which a linear, branched or cyclic hydrocarbon having 1 to 8 carbon atoms may be substituted on the nitrogen, a linear, branched or cyclic ether compound having 1 to 3 oxygen atoms in which a linear, branched or cyclic, saturated or unsaturated hydrocarbon having 1 to 8 carbon atoms may be each independently substituted on the oxygen atom(s), a linear, branched or cyclic ketone compound having 1 to 7 carbon atoms which may be substituted by an oxygen atom, a linear, branched or cyclic alkylnitrile having 1 to 6 carbon atoms, a linear, branched or cyclic, saturated or unsaturated halogenated hydrocarbon compound having 1 to 10 carbon atoms, and a linear or branched alcohol compound having 1 to 6 carbon atoms.

Such a solvent may be selected from, for example, toluene, o-xylene, m-xylene, p-xylene, 1,3,5-mesitylene, 1,2,3-mesitylene, 1,2,4-mesitylene, ethylbenzene, n-propylbenzene, i-propylbenzene, n-butylbenzene, i-butylbenzene, sec-butylbenzene, t-butylbenzene, n-pentylbenzene, i-pentylbenzene, sec-pentylbenzene, t-pentylbenzene, n-hexylbenzene, i-hexylbenzene, sec-hexylbenzene, t-hexylbenzene, cyclopentane, cyclohexane, cycloheptane, cyclooctane, methylcyclohexane, ethylcyclohexane, propylcyclohexane, n-butylcyclohexane, i-butylcyclohexane, sec-butylcyclohexane, t-butylcyclohexane, n-pentylcyclohexane, i-pentylcyclohexane, sec-pentylcyclohexane, t-pentylcyclohexane, n-hexylcyclohexane, i-hexylcyclohexane, sec-hexylcyclohexane, t-hexylcyclohexane, limonene, N,N'-dimethylformamide (DMF), N,N'-dimethylformacetamide (DMAc), 1,3-dimethyl-2-imidazolidinone (DMI), 1,3-dimethyl-3,4,5,6-tetrahydro-2(1H)-pyrimidinone (DMPU), diethyl ether, t-butyl methyl ether (TBME), dibutyl ether, cyclopentylmethyl ether (CPME), diphenyl ether, dimethoxymethane (DMM), 1,2-dimethoxyethane, diethylene glycol dimethyl ether, tetrahydrofuran (THF), tetrahydropyran (THP), dioxane, 2-methyltetrahydrofuran, 2-ethyltetrahydrofuran, acetone, methyl ethyl ketone (MEK), methyl isobutyl ketone (MIBK), cyclopentanone, cyclohexanone, cycloheptanone, acetonitrile, propionitrile, butyronitrile, $\alpha,\alpha,\alpha$-trifluoromethylbenzene, chlorobenzene, chloroform, dichloromethane, 1,2-dichloroethane, methanol, ethanol, 1-propanol, 2-propanol (IPA), n-butyl alcohol, i-butyl alcohol, sec-butyl alcohol, t-butyl alcohol, 1,2-ethylene glycol, 1,3-propylene glycol, 1,2-dihydroxypropane, 2-methoxyethanol and 2-(2-methoxyethoxy)ethanol, and more preferred is without solvent or toluene, ethylbenzene, methylcyclohexane, ethylcyclohexane, ethanol or IPA.

Incidentally, $R^{b2}$ in $R^B$ of the formula (1) is made a hydrocarbon group having 1 to 10 carbon atoms, the hydrogen atom in $R^B$ of the HB silicone obtained by the process may be substituted by the hydrocarbon group by a substitution reaction. By carrying out such a reaction, flexibility of the HB silicone can be adjusted.

The thus obtained HB silicone can be made a silicone modified composition containing a single polymer or a copolymer with the other polymerizable compound(s). The other polymerizable compound(s) is/are not particularly limited, and a suitable material may be used depending on the uses mentioned later.

Such a silicone modified composition may be suitably used as a paint, a device composition for eyes or a cosmetic composition. Among these, as the paint, there may be exemplified by a paint for stain proof and a transparent paint for an electronic material, and as the cosmetic composition, there may be exemplified by a composition for skin care, for hair, for antiperspirants, for deodorant, for makeup or for UV protection.

EXAMPLES

In the following, the present invention is explained by referring to Synthetic Examples and Examples, but the present invention is not limited by the following examples, and it is possible to carry out the invention by suitably modifying the same, either of which is also included in the technical scope of the present invention.

Incidentally, in the present Examples, the molecular structure was measured mainly by the nuclear magnetic resonance spectrometry ($^1$H-NMR, $^{13}$C-NMR) and infrared spectroscopy (IR), and the molecular weight distribution was measured by the gel permeation chromatography (hereinafter sometimes abbreviated to as GPC) measurement with a tetrahydrofuran (THF) solution.

Synthetic Example 1

Synthesis of $[[CH_2{=}CH(CH_2)_2OCH_2]_2CHOCH_2]_2CHOH$ $[[CH_2{=}CH(CH_2)_2OCH_2]_2CHOCH_2]_2CHOH$ was synthesized by two steps as mentioned above. First, as the first step, into a three-necked flask equipped with a thermometer, a stirring device and a nitrogen introducing tube were charged 3-buten-1-ol (3.5 mole), potassium hydroxide (3.2 mole) and tetrabutylammonium bromide (0.2 mole), and after the mixture was stirred at room temperature, epichlorohydrin (1.0 mole) charged in a dropping funnel was added dropwise to the mixture so that the inner temperature was kept at 45° C. After the dropping addition, the mixture was heated at 60° C. using an oil bath and stirred, and after disappearing $^1$H-NMR signal derived from glycidyl ether, neutralized by 4M hydrochloric acid, washed with water, treated by a saturated saline solution and by sodium sulfate, and filtered. The alcohol as the starting material was distilled off under reduced pressure, and the residue was distilled (130° C./600 Pa) to obtain a pale yellowish transparent oily product. Its spectroscopic data were $^1$H-NMR (400 MHz, $CDCl_3$) δ: 2.34 (tq, J=1.2, 6.7 Hz, 4H), 3.48 (dd, J=9.8, 6.3 Hz, 4H), 3.53 (dd, J=6.8, 1.6 Hz, 4H), 3.94 (ddd, J=11.6, 6.2, 3.8 Hz, 1H), 5.04 (dq, J=9.1, 1.6 Hz, 2H), 5.09 (dq, J=17.2, 1.7 Hz, 2H), 5.81 (ddd, J=17.2, 9.1, 6.7 Hz, 2H), $^{13}$C-NMR (100 MHz, $CDCl_3$) δ: 34.14 ($CH_2$×2), 69.50 (CH), 70.82 ($CH_2$×2), 71.94 ($CH_2$×2), 78.80 (CH×2), 116.56 ($CH_2$=CH×2), 135.16 ($CH_2$=CH×2), IR (NaCl) ν: 914, 995, 1023, 1112, 1382, 2864, 3077, 3442, and $[CH_2=CH(CH_2)_2OCH_2]_2CHOH$ (GDBE) could be synthesized with the yield of 82%.

Next, as the second step, in the method for preparing $[[CH_2=CH(CH_2)_2OCH_2]_2CHOCH_2]_2CHOH$ from the obtained GDBE, into a three-necked flask equipped with a thermometer, a stirring device and a nitrogen introducing tube were charged $[CH_2=CH(CH_2)_2OCH_2]_2CHOH$ (3.5 mole equivalent), potassium hydroxide (3.2 mole equivalent) and tetrabutylammonium bromide (0.2 mole), and after the mixture was stirred at room temperature, epichlorohydrin (1.0 mole equivalent) was added dropwise to the mixture so that the inner temperature did not exceed at 45° C. Thereafter, the mixture was heated at 60° C. using an oil bath and stirred, neutralized by 4M hydrochloric acid, washed with water, treated by a saturated saline solution and by sodium sulfate, and filtered. Then, $[CH_2=CH(CH_2)_2OCH_2]_2CHOH$ was distilled off under reduced pressure (130° C./600 Pa) to obtain a colorless transparent oily product. Its spectroscopic data were $^1$H-NMR (400 MHz, $CDCl_3$) δ: 2.35 (tq, J=1.3, 6.7 Hz, 8H), 3.42-3.84 (m, 24H), 3.93 (ddd, J=11.6, 6.1, 3.7 Hz, 1H), 5.03 (dq, J=9.0, 1.6 Hz, 4H), 5.09 (dq, J=17.3, 1.3 Hz, 4H), 5.83 (ddd, J=17.3, 9.0, 6.7 Hz, 4H), $^{13}$C-NMR (100 MHz, $CDCl_3$) δ: 34.16 ($CH_2$×4), 69.51 (CH), 70.80 ($CH_2$×4), 71.95 ($CH_2$×4), 78.68 (CH×2), 116.56 ($CH_2$=CH×4), 135.20 ($CH_2$=CH×2).

IR (NaCl) ν: 915, 997, 1021, 1112, 1383, 2865, 3076, 3441, and $[[CH_2=CH(CH_2)_2OCH_2]_2CHOCH_2]_2CHOH$ could be synthesized with the yield of 79%.

Synthetic Example 2

Synthesis of $[[CH_2=C(CH_3)(CH_2)_2OCH_2]_2CHOCH_2]_2CHOH$ (GDiPE)

In the same manner as in Synthetic Example 1 except for changing 3-buten-1-ol in the first step of Synthetic Example 1 to 3-methyl-3-buten-1-ol (isoprenol), a pale yellowish transparent oily product was obtained. Its spectroscopic data were $^1$H-NMR (400 MHz, $CDCl_3$) δ: 2.34 (tq, J=1.2, 6.7 Hz, 4H), 3.48 (dd, J=9.8, 6.3 Hz, 4H), 3.53 (dd, J=6.8, 1.6 Hz, 4H), 3.94 (ddd, J=11.6, 6.2, 3.8 Hz, 1H), 5.04 (dq, J=9.1, 1.6 Hz, 2H), 5.09 (dq, J=17.2, 1.7 Hz, 2H), 5.81 (ddd, J=17.2, 9.1, 6.7 Hz, 2H), $^{13}$C-NMR (100 MHz, $CDCl_3$) δ: 34.14 ($CH_2$×2), 69.50 (CH), 70.82 ($CH_2$×2), 71.94 ($CH_2$×2), 78.80 (CH×2), 116.56 ($CH_2$=CH×2), 135.16 ($CH_2$=CH×2), IR (NaCl) ν: 914, 995, 1023, 1112, 1382, 2864, 3077, 3442, and $[CH_2=C(CH_3)(CH_2)_2OCH_2]_2CHOH$(GDiPE) could be synthesized with the yield of 80%.

Next, as the second step, in the same manner as mentioned above except for changing GDBE of Synthetic Example 1 to GDiPE obtained in the Synthetic Example 2, a colorless transparent oily product was obtained. Its spectroscopic data were $^1$H-NMR (400 MHz, $CDCl_3$) δ: 1.71 (s, 6H), 2.35 (tq, J=1.3, 6.7 Hz, 8H), 3.42-3.84 (m, 24H), 3.93 (ddd, J=11.6, 6.1, 3.7 Hz, 1H), 4.87 (s, 4H), 4.93 (s, 4H), $^{13}$C-NMR (100 MHz, $CDCl_3$) δ: 34.16 ($CH_2$×4), 69.51 (CH), 70.80 ($CH_2$×4), 71.95 ($CH_2$×4), 78.68 (CH×2), 116.56 ($CH_2$=CH×4), 135.20 ($CH_2$=CH×2), IR (NaCl) ν: 915, 997, 1021, 1112, 1383, 2865, 3076, 3441, and $[[CH_2=C(CH_3)(CH_2)_2OCH_2]_2CHOCH_2]_2CHOH$ could be synthesized with the yield of 78%.

Synthetic Example 3

Into 100 mL of a three-necked flask equipped with a thermometer, a magnetic stirrer bar and a nitrogen introducing tube were charged 20.0 g (43.8 mole) of $[[CH_2=CH(CH_2)_2OCH_2]_2CHOCH_2]_2CHOH$ synthesized in the Synthetic Example 1, 0.79 mg (0.005 mole %) of iron acetylacetonate [Fe(acac)$_3$] catalyst available from Dojindo Laboratories and 2.70 mg (100 ppm) of BHT, and the mixture was heated to 40° C. while stirring. To the mixture was added dropwise 7.14 g (46.0 mole) of Karenz MCI charged in a dropping funnel so that the inner temperature did not exceed at 45° C. The mixture was stirred at the same temperature for 30 minutes, and when the signal (5.00 ppm) derived from the carbamic acid ester was confirmed to be formed with a hydrogen ratio of 1H by $^1$H-NMR, the reaction temperature was returned to room temperature, 81 mg (0.3 wt %) of activated charcoal was added to the mixture, and the resulting mixture was stirred at room temperature for one hour. Thereafter, the activated charcoal was filtered off, and slightly excessive Karenz MCI was distilled off under reduced pressure (90 to 100° C./<1 KPa) to obtain a pale yellowish transparent oily product. The spectroscopic data of the obtained product were $^1$H-NMR (400 MHz, $CDCl_3$) δ: 1.95 (t, J=1.2 Hz, 3H), 2.31 (dt, J=6.7, 1.3 Hz, 8H), 3.42-3.84 (m, 24H), 4.21 (t, J=5.3 Hz, 2H), 5.49-5.51 (m, 10H), 5.59 (t, J=1.2 Hz, 1H), 5.80 (ddt, J=17.0, 10.3, 6.7 Hz, 4H), 6.11 (s, 1H), $^{13}$C-NMR (75 MHz, $CDCl_3$) δ: 34.15 ($CH_2$×4), 40.66 ($CH_2$), 69.50 (CH), 70.84 ($CH_2$×2), 70.87 ($CH_2$×4), 71.68 ($CH_2$), 71.96 ($CH_2$×4), 78.67 (CH×2), 116.55 ($CH_2$=CH×4), 125.28 ($CH_2$=C($CH_3$)), 135.25 ($CH_2$=CH×4), 135.99 ($CH_2$=C($CH_3$)), 155.72 (C=O), 166.63 (C=O), IR (NaCl) ν: 798, 840, 1033, 1160, 1259, 1725, 2926, 2959, 3356, and $[[CH_2-CH(CH_2)_2OCH_2]_2CHOC(=O)NH(CH_2)_2OC(=O)C(CH_3)-CH_2$ could be obtained with the yield of 89%.

Synthetic Example 4

The reaction was carried out under the same conditions as in Synthetic Example 3 except for changing $[[CH_2=CH(CH_2)_2OCH_2]_2CHOCH_2]_2CHOH$ in the Synthetic Example 3 to $[[CH_2=C(CH_3)(CH_2)_2OCH_2]_2CHOCH_2]_2CHOH$ synthesized in the Synthetic Example 2 to obtain a pale yellowish transparent oily product. The spectroscopic data of the obtained product were $^1$H-NMR (400 MHz, $CDCl_3$) δ: 1.72 (s, 12H), 1.95 (t, J=1.2 Hz, 3H), 2.31 (dt, J=6.7, 1.3 Hz. 8H), 3.42-3.84 (m, 24H), 4.21 (t, J=5.3 Hz, 2H), 4.87 (s, 4H), 4.94 (s, 4H), 5.49-5.51 (m, 6H), 5.59 (t, J=1.2 Hz, 1H), 6.11 (s, 1H), $^{13}$C-NMR (75 MHz, $CDCl_3$) δ: 34.15 ($CH_2$×4), 40.66 ($CH_2$), 69.50 (CH), 70.84 ($CH_2$×2), 70.87 ($CH_2$×4), 71.68 ($CH_2$), 71.96 ($CH_2$×4), 78.67 (CH×2), 116.55 ($CH_2$=CH×4), 125.28 ($CH_2$=C($CH_3$)), 135.25 ($CH_2$=CH×4), 135.99 ($CH_2$=C($CH_3$)), 155.72 (C=O), 166.63 (C=O), IR (NaCl) ν: 798, 840, 1033, 1160, 1259, 1725, 2926, 2959, 3356, and $[[CH_2=C(CH_3)(CH_2)_2OCH_2]_2CHOC(=O)NH(CH_2)_2OC(-O)C(CH_3)=CH_2$ could be obtained with the yield of 82%.

Synthetic Example 5

In the same molar ratio and operating procedure as in Synthetic Example 3 except for changing $[[CH_2{=}CH(CH_2)_2OCH_2]_2CHOCH_2]_2CHOH$ of Synthetic Example 3 to $[[CH_2{=}CHCH_2OCH_2]_2CHOCH_2]_2CHOH$(GDAE), a pale yellowish transparent oily product was obtained. The spectroscopic data of the obtained product were $^1$H-NMR (400 MHz, $CDCl_3$) δ: 1.95 (t, J=1.2 Hz, 3H), 3.40-3.85 (m, 24H), 4.21 (t, J=5.4 Hz, 2H), 5.49-5.52 (m, 10H), 5.60 (t, J=1.4 Hz, 1H), 5.85 (ddt, J=17.0, 10.3, 6.7 Hz, 4H), 6.10 (s, 1H), $^{13}$C-NMR (75 MHz, $CDCl_3$) δ: 40.70 ($CH_2$), 69.53 (CH), 70.84 ($CH_2$×2), 70.91 ($CH_2$×4), 71.67 ($CH_2$), 71.95 ($CH_2$×4), 78.68 (CH×2), 116.33 ($CH_2{=}CH$×4), 125.30 ($CH_2{=}C(CH_3)$) 135.21 ($CH_2{=}CH$×4), 136.00 ($CH_2{=}C(CH_3)$), 155.73 (C=O), 166.64 (C=O), IR (NaCl) ν: 797, 843, 1034, 1163, 1261, 1726, 2931, 2966, 3433, and $[[CH_2{=}CHCH_2OCH_2]_2CHOC({=}O)NH(CH_2)_2OC({=}O)C(CH_3){=}CH_2$ could be obtained with the yield of 92%.

Example 1

In 100 mL of a three-necked flask equipped with a thermometer, a magnetic stirrer bar and a nitrogen introducing tube were charged 18.3 g (29.9 mmole) of $[[CH_2{=}CH(CH_2)_2OCH_2]_2CHOC({=}O)NH(CH_2)_2OC({=}O)C(CH_3){=}CH_2$ synthesized in Synthetic Example 1, 7.91 mg (100 ppm) of BHT and 23.6 g (30 wt %) of toluene, and a dropping funnel in which 45.0 g (109 mmole) of 1-butyl-9-hydro-1,1,3,3,5,5,7,7,9,9-decamethylpentasiloxane has been charged was mounted to the flask, then, the mixture was heated to 60° C. under stirring. To the mixture was added 47.4 mg (3 ppm) of 0.5 wt % toluene solution containing a Karstedt's catalyst ($Pt_2[[(CH_2{=}CH)(CH_3)_2Si]_2O]_3$) by microsyringe, the mixture was stirred at the same temperature for 10 minutes, and then, H-siloxane was added dropwise to the mixture so that the inner temperature did not exceed at 65° C. When the mixture was measured by $^1$H-NMR after ceasing exothermic reaction, then the signal of the olefin was confirmed to be disappeared. Thereafter, the reaction temperature was returned to room temperature, 0.24 g (0.3 wt %) of activated charcoal was added to the mixture, and the resulting mixture was stirred at room temperature for one hour. After the activated charcoal was filtered off, toluene was distilled off under reduced pressure (100° C./<1 KPa) to obtain a pale yellowish transparent oily product. The spectroscopic data of the obtained product were the molecular weight distribution Mw/Mn=1.03, $^1$H-NMR (400 MHz, $CDCl_3$) δ: 0.03-0.08 (m, 160H), 0.48-0.58 (m, 16H), 0.88 (t, J=7.1 Hz, 12H), 1.24-1.42 (m, 24H), 1.57 (quin., J=7.0 Hz, 8H), 1.94 (s, 3H), 3.30-3.84 (m, 24H), 4.21 (t, J=5.2 Hz, 2H), 4.88-5.08 (m, 2H), 5.58 (t, J=1.5 Hz, 1H), 6.11 (s, 1H), $^{13}$C-NMR (100 MHz, $CDCl_3$) δ: 0.03 ($CH_3$×16), 0.62 ($CH_3$×8), 0.79 ($CH_3$×16), 13.40 ($CH_2$×4), 17.77 ($CH_2$×4), 17.81 ($CH_2$×4), 19.50 ($CH_2$×4), 25.31 ($CH_2$×4), 26.01 ($CH_2$×4), 33.05 ($CH_2$×4), 40.61 ($CH_2$), 69.54 (CH), 70.81 ($CH_2$×2), 71.71 ($CH_2$), 71.93 ($CH_2$×4), 78.71 (CH×2), 125.33 ($CH_2{=}C(CH_3)$), 135.96 ($CH_2{=}C(CH_3)$), 155.71 (C=O), 166.71 (C=O).

IR (NaCl) ν: 797, 839, 1031, 1159, 1261, 1728, 2924, 2959, 3353, and $[[Bu[Si(CH_3)_2O]_4Si(CH_3)_2(CH_2)_4OCH_2]_2CHOCH_2]_2CHOC({=}O)NH(CH_2)_2OC({=}C)C(CH_3){=}CH_2$ could be obtained with the yield of 90%.

Example 2

In the same molar ratio and operating procedure as in Example 1 except for changing 1-butyl-9-hydro-1,1,3,3,5,5,7,7,9,9-decamethylpentasiloxane in Example 1 to 3-hydro-1,1,1,3,5,5-heptamethyltrisiloxane, a pale yellowish transparent oily product was obtained. The spectroscopic data of the obtained product were the molecular weight distribution Mw/Mn=1.05, $^1$H-NMR (400 MHz, $CDCl_3$) δ: −0.02 (s, 12H), 0.04-0.15 (m, 72H), 0.35-0.50 (m, 8H), 1.45-1.65 (m, 8H), 1.92 (s, 3H), 3.30-3.85 (m, 24H), 4.22 (t, J=5.2 Hz, 2H), 4.90-5.10 (m, 2H), 5.59 (t, J=1.5 Hz, 1H), 6.10 (s, 1H), $^{13}$C-NMR (100 MHz, $CDCl_3$) δ: −0.56 ($CH_3$×4), 1.53 ($CH_3$×24), 13.30 ($CH_2$×4), 17.89 ($CH_3$), 23.01 ($CH_2$×4), 40.59 ($CH_2$), 69.56 (CH), 70.82 ($CH_2$×2), 71.72 ($CH_2$), 71.95 ($CH_2$×4), 78.69 (CH×2), 125.35 ($CH_2{=}C(CH_3)$), 135.98 ($CH_2{=}C(CH_3)$), 155.73 (C=O), 166.68 (C=O), IR (NaCl) ν: 798, 841, 1033, 1161, 1259, 1726, 2925, 2962, 3356, and $[[[Si(CH_3)_3O]_2Si(CH_3)(CH_2)_4OCH_2]_2CHOCH_2]_2CHOC({=}O)NH(CH_2)_2OC({=}O)C(CH_3){=}CH_2$ could be synthesized with the yield of 92%.

Example 3

In the same molar ratio and operating procedure as in Example 1 except for changing $[[CH_2{-}CH(CH_2)_2OCH_2]_2CHOC({=}O)NH(CH_2)_2OC({=}O)C(CH_3){=}CH_2$ (Synthetic Example 1) in Example 1 to $[CH_2{=}C(CH_3)(CH_2)_2OCH_2]_2CHOC({=}O)NH(CH_2)_2OC({=}O)C(CH_3){=}CH_2$ obtained in Synthetic Example 4, a pale yellowish transparent oily product was obtained. The spectroscopic data of the obtained product were the molecular weight distribution Mw/Mn=1.03, $^1$H-NMR (400 MHz, $CDCl_3$) δ: 0.03-0.08 (m, 160H), 0.44-0.58 (m, 16H), 0.65 (q, J=14.7, 4.9 Hz, 8H), 0.88 (t, J=7.1 Hz, 12H), 0.94 (d, J=6.6 Hz, 12H), 1.24-1.42 (m, 20H), 1.57 (quip., J=7.0 Hz, 8H), 1.94 (s, 3H), 3.30-3.84 (m, 24H), 4.21 (t, J=5.2 Hz, 2H), 4.88-5.08 (m, 2H), 5.58 (t, J=1.5 Hz, 1H), 6.11 (s, 1H), $^{13}$C-NMR (100 MHz, $CDCl_3$) δ: 0.03 ($CH_3$×16), 0.62 ($CH_3$×8), 0.79 ($CH_3$×16), 11.90 ($CH_3$×4), 17.77 ($CH_2$×4), 17.81 ($CH_2$×4), 19.50 ($CH_2$×4), 25.31 (CH×4), 26.01 ($CH_2$×4), 33.05 ($CH_2$×4), 40.61 ($CH_2$), 69.54 (CH), 70.81 ($CH_2$×2), 71.71 ($CH_2$), 71.93 ($CH_2$×4), 78.71 (CH×2), 125.33 ($CH_2{=}C(CH_3)$), 135.96 ($CH_2{=}C(CH_3)$), 155.71 (C=O), 166.71 (C=O), IR (NaCl) ν: 797, 839, 1031, 1159, 1261, 1728, 2924, 2959, 3353, and $[[Bu[Si(CH_3)_2O]_4Si(CH_3)_2(CH_2)_4OCH_2]_2CHOCH_2]_2CHOC({=}O)NH(CH_2)_2OC({=}O)C(CH_3){=}CH_2$ could be obtained with the yield of 90%.

Example 4

In the same molar ratio and operating procedure as in Example 1 except for changing $[[CH_2{=}CH(CH_2)_2OCH_2]_2CHOC({=}O)NH(CH_2)_2OC({=}O)C(CH_3){=}CH_2$ (Synthetic Example 1) in Example 1 to $[[CH_2{=}CHCH_2OCH_2]_2CHOC({=}O)NH(CH_2)_2OC({=}O)C(CH_3){=}CH_2$ obtained in Synthetic Example 5, a pale yellowish transparent oily product was obtained. The spectroscopic data of the obtained product were $^1$H-NMR (400 MHz, $CDCl_3$) δ: 0.02-0.10 (m, 120H), 0.46-0.58 (m, 16H), 0.88 (t, J=6.9 Hz, 12H), 1.25-1.37 (m, 16H), 1.49-1.63 (m, 16H), 1.94 (s, 3H), 3.33-3.86 (m, 24H), 4.21 (q, J=4.7 Hz, 2H), 4.90-5.07 (m, 2H), 5.59 (t, J=1.5 Hz, 1H), 6.11 (s, 1H), $^{13}$C-NMR (75 MHz, $CDCl_3$) δ: 0.00 ($CH_3$×16), 0.63 ($CH_3$×8), 0.81 ($CH_3$×16), 13.43 ($CH_2$×4), 17.76 ($CH_2$×4), 19.51 ($CH_2$×4), 25.33 ($CH_2$×4), 26.03 ($CH_2$×4), 33.09 ($CH_2$×4), 40.51 ($CH_2$), 69.50 (CH), 70.83 ($CH_2$×2), 71.76 ($CH_2$), 71.89 ($CH_2$×4), 78.78 (CH×2), 125.36 ($CH_2$=C($CH_3$)), 135.91 ($CH_2$=C($CH_3$)), 155.77 (C=O), 166.73 (C=O), IR (NaCl) ν: 798, 840, 1033, 1160, 1259, 1725, 2926, 2959, 3356, and $[[Bu[Si(CH_3)_2O]_4Si(CH_3)_2(CH_2)_3OCH_2]_2CHOCH_2]_2CHOC(=O)NH(CH_2)_2OC(=O)C(CH_3)=CH_2$ could be obtained with the yield of 80%.

Example 5

In the same molar ratio and operating procedure as in Example 2 by using $[[CH_2=CHCH_2OCH_2]_2CHOC(=O)NH(CH_2)_2OC(=O)C(CH_3)=CH_2$ obtained in Synthetic Example 5, a pale yellowish transparent oily product was obtained. The spectroscopic data of the obtained product were the molecular weight distribution Mw/Mn=1.06, $^{1}$H-NMR (400 MHz, $CDCl_3$) δ: 0.01 (s, 12H), 0.08 (s, 72H), 0.43 (t, J=8.3 Hz, 8H), 1.44-1.65 (m, 16H), 1.95 (s, 3H), 3.28-3.86 (m, 24H), 4.22 (q, J=5.0 Hz, 2H), 4.90-5.08 (m, 2H), 5.59 (t, J=1.5 Hz, 1H), 6.11 (s, 1H), $^{13}$C-NMR (75 MHz, $CDCl_3$) δ: −0.73 ($CH_3$×4), 1.45 ($CH_3$×24), 13.28 ($CH_2$×4), 17.83 ($CH_2$), 22.95 ($CH_2$×4), 39.85 ($CH_2$), 63.28 (CH), 69.02 ($CH_2$×4), 71.67 ($CH_2$), 73.60 (CH×2), 73.68 ($CH_2$×4), 78.40 ($CH_2$×2), 125.13 ($CH_2$=C($CH_3$)), 135.79 ($CH_2$=C), 155.61 (C=O), 166.46 (C=O), IR (NaCl) ν: 914, 995, 1023, 1112, 1382, 1724, 2864, 3077, 3442, and $[[Bu[Si(CH_3)_2O]_4Si(CH_3)_2(CH_2)_3OCH_2]_2CHOCH_2]_2CHOC(=O)NH(CH_2)_2OC(=O)C(CH_3)=CH_2$ could be obtained with the yield of 84%.

$^{1}$H-NMR, $^{13}$C-NMR or IR of Examples 1 to 3 were shown a product of four chains of the silicone as a main product, but whole of three chains or two chains of silicones in which the double bond was internally rearranged which were by-products could not be assigned in NMR or IR since the amounts produced were a little. In Examples 4 and 5, a product of four chains of the silicone was not a main product, but NMR was read and assigned. By GPC measurement using the THF solvent, an amount of an internal rearrangement product of the olefin was measured. The results are shown in Table 1. In Examples 4 and 5 in which an allyl group was used, whereas internal rearrangement of the olefin was generated, a product into which four siloxane chains have been introduced could be obtained while it was a small amount. In addition, in Examples 1 and 2 in which a 3-butenyl group was used or in Example 3 in which an isoprenyl group was used, a symmetric hyperbranched compound into which four siloxane chains have been introduced could be prepared as a main product with higher purity than those of Example 4 and 5.

TABLE 1

| | Number of siloxane chains | | | | |
|---|---|---|---|---|---|
| | 4 | 3 | 2 | 1 | 0 |
| Example 1 | 90 | 9 | 1 | — | — |
| Example 2 | 89 | 14 | 2 | — | — |
| Example 3 | 100 | — | — | — | — |
| Example 4 | 5 | 44 | 36 | 14 | 1 |
| Example 5 | 4 | 9 | 60 | 18 | 9 |

The HB silicone thus obtained has flexibility in its branched skeleton itself than the conventional ones, and has good reactivity of the polymerizable functional group, while it is a highly branched structure having a siloxane chain.

It must be stated here that the present invention is not restricted to the embodiments shown by the embodiments. The embodiments are merely examples so that any embodiments composed of substantially the same technical concept as disclosed in the claims of the present invention and expressing a similar effect are included in the technical scope of the present invention.

INDUSTRIAL APPLICABILITY

According to the present invention, a symmetric hyperbranched type silicone-modified polymerizable compound which is useful for a paint, a device composition for eyes, or a cosmetic composition including for skin care, hair, antiperspirants, deodorant, makeup or UV protection, etc., and its modularized preparation method are provided.

The invention claimed is:

1. A symmetric hyperbranched type silicone-modified polymerizable compound which comprises a compound represented by the following general formula (1), $$[(R^AR^B)_2CHOCH_2]_2CHOR^C{}_cR^D \quad (1)$$

wherein $R^A$ represents a monovalent linear, branched or cyclic siloxane chain;

$R^B$ represents a divalent hydrocarbonylene methylene ether group represented by $-CH_2CR^{b1}R^{b2}(CR^{b3}R^{b4})_{n1}OCH_2-$, each of $R^{b1}$, $R^{b2}$, $R^{b3}$ and $R^{b4}$ may be the same or different from each other and represents a hydrogen atom or a linear, branched or cyclic hydrocarbon group having 1 to 10 carbon atoms which may be bonded to each other, "n1" represents an integer selected from 0 to 10; $R^C$ represents a divalent linking group; "c" represents 0 or 1; and $R^D$ represents an unsaturated polymerizable functional group.

2. The symmetric hyperbranched type silicone-modified polymerizable compound according to claim 1, wherein in the divalent hydrocarbonylene methylene ether group represented by $R^B$ in the general formula (1), "n1" represents an integer selected from 1 to 10, and when "n1" represents 1, $R^{b1}$ represents a hydrocarbon group having 1 to 10 carbon atoms and $R^{b2}$ represents a hydrogen atom.

3. The symmetric hyperbranched type silicone-modified polymerizable compound according to claim 1, wherein the divalent linking group represented by $R^C$ in the general formula (1) is any of linking groups selected from divalent linking groups represented by $-XR^Y{}_yR^ZO-$, $-XR^Y{}_yCR^{Z'}R^{Z''}O-$, and an oligoalkylene oxy group having a repeating unit whose number of repetition is an integer of 1 to 10, the repeating unit having 2 to 10 carbon atoms, wherein X represents any one selected from $-CH_2-$, $-C(=O)-$ and $-C(=S)-$, $R^Y$ represents a divalent functional group containing 0 or 1 atom selected from a nitrogen atom, an oxygen atom, a sulfur atom or a carbon atom, $R^Z$ represents a linear, branched or cyclic alkylene group having 2 to 10 carbon atoms which may be substituted by an oxygen atom(s), "y" represents an integer selected from 0 or 1, $R^{Z'}$ and $R^{Z''}$ each represent an alkyl group having 1 to 10 carbon atoms.

4. The symmetric hyperbranched type silicone-modified polymerizable compound according to claim 2, wherein the divalent linking group represented by $R^C$ in the general formula (1) is any of linking groups selected from divalent linking groups represented by —$XR^Y{}_yR^ZO$—, —$XR^Y{}_yCR^{Z'}R^{Z''}O$—, and an oligoalkylene oxy group having a repeating unit whose number of repetition is an integer of 1 to 10, the repeating unit having 2 to 10 carbon atoms, wherein X represents any one selected from —$CH_2$—, —C(═O)— and —C(═S)—, $R^Y$ represents a divalent functional group containing 0 or 1 atom selected from a nitrogen atom, an oxygen atom, a sulfur atom or a carbon atom, $R^Z$ represents a linear, branched or cyclic alkylene group having 2 to 10 carbon atoms which may be substituted by an oxygen atom(s), "y" represents an integer selected from 0 or 1, $R^{Z'}$ and $R^{Z''}$ each represent an alkyl group having 1 to 10 carbon atoms.

5. A process for preparing the symmetric hyperbranched type silicone-modified polymerizable compound according to claim 1, a modularized preparation method of which comprises subjecting a compound represented by the following general formula (2) and an intermediate represented by the following general formula (3) to a hydrosilylation reaction to prepare the compound represented by the general formula (1), $$R^{A'} \quad (2)$$

wherein $R^{A'}$ represents a linear, branched or cyclic siloxane having one reactive hydrogen group in the molecule, $$(R^{B'}{}_2CHOCH_2)_2CHOR^C{}_cR^D \quad (3)$$

wherein $R^{B'}$ represents a monovalent hydrocarbonylene methylene ether group having a double bond at the terminal thereof and represented by $CH_2{=}CR^{b1}(CR^{b3}R^{b4})_{n1'}OCH_2$—, where $R^{b1}$, $R^{b3}$ and $R^{b4}$ have the same meanings as defined above, "n1'" represents an integer selected from 0 to 10; and $R^C$, "c" and $R^D$ have the same meanings as defined above.

6. The modularized preparation method according to claim 5, wherein "n1'" in the general formula (3) is an integer selected from 1 to 10.

7. The modularized preparation method according to claim 5, wherein a catalyst is used in the hydrosilylation reaction, and the compound represented by the general formula (2) is used in an amount of 0.80 to 1.00 mole % based on the terminal alkenyl group of the intermediate represented by the general formula (3).

8. The modularized preparation method according to claim 6, wherein a catalyst is used in the hydrosilylation reaction, and the compound represented by the general formula (2) is used in an amount of 0.80 to 1.00 mole % based on the terminal alkenyl group of the intermediate represented by the general formula (3).

9. The modularized preparation method according to claim 7, wherein the catalyst to be used in the hydrosilylation reaction is a transition metal catalyst.

10. The modularized preparation method according to claim 8, wherein the catalyst to be used in the hydrosilylation reaction is a transition metal catalyst.

11. The modularized preparation method according to claim 9, wherein the transition metal catalyst is a platinum catalyst.

12. The modularized preparation method according to claim 10, wherein the transition metal catalyst is a platinum catalyst.

13. The modularized preparation method according to claim 5, wherein the intermediate represented by the general formula (3) is prepared by reacting the compound represented by the following general formula (4) and the compound represented by the following general formula (5) or the compound represented by the following general formula (6), $$(R^{B'}{}_2CHOCH_2)_2CHOH \quad (4)$$

wherein $R^{B'}$ has the same meaning as defined above, $$R^{C'}R^D \quad (5)$$

wherein $R^D$ has the same meaning as defined above, and $R^{C'}$ represents a monovalent reactive group, $$R^{D'} \quad (6)$$

wherein $R^{D'}$ represents an unsaturated polymerizable compound having a reactive functional group.

14. The modularized preparation method according to claim 13, wherein the monovalent reactive group represented by $R^{c'}$ in the general formula (5) is any of the reactive group selected from a monovalent reactive group represented by $X{=}R^{Y'}R^ZO$—, T-X—$R^Y{}_yR^ZO$—, $X{=}R^{Y'}CR^{Z'}R^{Z''}O$—, T-X—$R^Y{}_yCR^{Z'}R^{Z''}O$—, and an oligoalkyleneoxy group having a repeating unit whose number of repetition is an integer of 1 to 10, the repeating unit having 2 to 10 carbon atoms, which has a reactive group at the one terminal, wherein X, $R^Y$, $R^Z$, "y", $R^{Z'}$ and $R^{Z''}$ have the same meanings as defined above, $R^{Y'}$ represents a trivalent functional group containing 0 or 1 of any atom selected from a nitrogen atom, an oxygen atom, a sulfur atom and a carbon atom, and T represents a hydroxyl group or any atom selected from a chlorine atom and a bromine atom.

15. The modularized preparation method according to claim 13, wherein $R^D$ in the general formula (5) is a monovalent unsaturated polymerizable functional group selected from any of an acrylic group, a methacrylic group, an alkynyl group, a styryl group, an indenyl group, an alkenyl group, a cycloalkenyl group, a norbornyl group, a conjugated or non-conjugated alkadiene group and a vinyl ether group each of which may contain a linear, branched or cyclic substituent having 1 to 10 carbon atoms which contains a hetero atom(s).

16. The modularized preparation method according to claim 14, wherein $R^D$ in the general formula (5) is a monovalent unsaturated polymerizable functional group selected from any of an acrylic group, a methacrylic group, an alkynyl group, a styryl group, an indenyl group, an alkenyl group, a cycloalkenyl group, a norbornyl group, a conjugated or non-conjugated alkadiene group and a vinyl ether group each of which may contain a linear, branched or cyclic substituent having 1 to 10 carbon atoms which contains a hetero atom(s).

17. The modularized preparation method according to claim 13, wherein $R^{D'}$ of the general formula (6) is an unsaturated polymerizable compound which contains a material in which an unsaturated group selected from any of an acrylic group, a methacrylic group, an alkynyl group, a styryl group, an indenyl group, an alkenyl group, a cycloalkenyl group, a norbornyl group, a conjugated or non-conjugated alkadiene group and a vinyl ether group each of which may contain a linear, branched or cyclic substituent having 1 to 10 carbon atoms which contains a hetero atom(s), and a reactive functional group selected from any of a hydroxyl group, an amino group, a hydroxycarbonyl group, an aldehyde group, an acid halide group, an ester group, a haloformate group, a halogenated alkyl group, an isocyanate group, an isothiocyanate group, a ketene group, a phosphate group, an epoxy group, an aziridine group, a tosyl group, a mesyl group, a trifluoromethanesulfonyl group, a bromane group, an iodane group, a halogenated aryl group and a nitroaryl group are directly bonded, or bonded through a linking group in the molecule.

18. The modularized preparation method according to claim 13, wherein one or more kinds of catalysts comprising a Lewis acid selected from any of an inorganic or organic tin complex, titanium complex, iron complex, copper complex, zinc complex, aluminum complex, zirconium complex, yttrium complex, scandium complex, indium complex, lanthanum complex, cerium complex, samarium complex, europium complex and silicon complex; or a tertiary organic base is used in the reaction of the compound represented by the general formula (4) and the compound represented by the general formula (5) or the compound represented by the general formula (6), and the catalyst is used in an amount of 0.001 to 0.500 mole % based on an amount of the compound represented by the general formula (4).

* * * * *